United States Patent [19]

Eckardt et al.

[11] Patent Number: 4,960,694
[45] Date of Patent: Oct. 2, 1990

[54] TEST COMBINATION AND METHOD OF DETECTING FIBRIN MONOMERS IN BLOOD

[76] Inventors: Klaus Eckardt, Erfurter Strasse 58, 6900 Jena; Gottfried Toepfer, Am Feierabendheim 26, 8909 Goerlitz; Andreas Seifert, Theodor-Koerner-Strasse 5, 8900 Goerlitz; Manfred Schulze, Ludwigstrasse 2; Udo Funke, Rietschelstrasse 20, both of 8800 Zittau; Marlena Stepanauskas, deceased, late of Berlin; by Leonas-Vitas Stepanauskas, and Daina Stepanauskas, legal representatives, both of Rudolf-Reusch-Str. 43, 1156 Berlin; Heinz Thrum, deceased, late of Jena; by Margot Thrum, legal representative, Hermann-Löns-Str. 62, 6900 Jena; by Matthias Thrum, legal representative, Thomas-Mann-Str. 3, Schleiz; by Michael Thrum, legal representative, Hermann-Löns-Str. 62, Jena, all of German Democratic Rep.

[21] Appl. No.: 71,799

[22] Filed: Jul. 9, 1987

[30] Foreign Application Priority Data

Jul. 9, 1986 [DD] German Democratic Rep. .................................... 2922981

[51] Int. Cl.$^5$ .................... G01N 33/68; G01N 33/86

[52] U.S. Cl. .................... 435/13; 436/63; 436/69; 424/116; 424/121; 424/122; 514/422; 548/518

[58] Field of Search .................... 435/13; 436/63, 69; 424/116, 121, 122; 514/422; 548/518

[56] References Cited

U.S. PATENT DOCUMENTS

| | | | |
|---|---|---|---|
| 3,990,947 | 11/1976 | Butler et al. | 435/13 |
| 4,145,185 | 3/1979 | Brinkhous et al. | 436/69 |
| 4,210,420 | 7/1980 | Baughman et al. | 436/69 |
| 4,429,040 | 1/1984 | Becker et al. | 435/13 X |
| 4,692,406 | 9/1987 | Becker et al. | 435/13 |
| 4,710,459 | 12/1987 | Bartl et al. | 435/13 |
| 4,766,142 | 8/1988 | Arcamone et al. | 514/422 |

OTHER PUBLICATIONS

Patel, D., "Antibiotic-DNA Interactions: Intermolecular Nuclear Overhauser Effects in the Netropsin-d(-C-G-C-G-A-A-T-T-C-G-C-G) Complex in Solution", Proc. Natl. Acad. Sci., U.S.A., vol. 79, pp. 6424–6428, Nov. 1982.
Biological Abstract 85:13421.

Primary Examiner—Elizabeth C. Weimar
Assistant Examiner—Carol Spiegel

[57] ABSTRACT

A test reagent for detecting fibrin monomers in blood, comprises an antibiotic of a pyrrole amidine series as a precipitant, introduced in a buffer solution. A method of detecting fibrin monomers in blood, comprises the steps of mixing venous blood with an anticoagulant, centrifuging the mixture of the venous blood with the anticoagulant, removing a citrate plasma, using an antibiotic of a pyrrole amidine series as a precipitant, and evaluating a precipitation reaction which takes place thereby.

4 Claims, No Drawings

TEST COMBINATION AND METHOD OF DETECTING FIBRIN MONOMERS IN BLOOD

BACKGROUND OF THE INVENTION

The present invention relates to a test reagent for detecting fibrin monomers and a method of detecting the same in human blood plasma.

The appearance of fibrin monomers in blood is a proof of an activation of the hemostasis system. This is a clinically frequently occurring symptom of many basic illnesses. Therefore, after the hypercoagulation stage, locally caused thromboses or generally coagulation pathologies can develop with resulting heavy bleeding. The possible early detection of coagulating activity is a prerequisite for an effective therapy.

Several principles for detecting the fibrin monomers are known in the art. The oldest methods include the ethanol-gelatin test in accordance with GODAL (H. GODAL and U. ABILGAARD, Scand. J. Haem. 3, 1966, 342) and the protamine sulfate test in accordance with LIPPINSKI (B. LIPPINSKI and K. WAROWSKI, Thromb. Diath. Haem. 20, 1968, 44). These methods are easy to carry out. However, they show an insufficient sensitivity and specificity. A specific test is the agglutination test with fibrin monomer loaded erythrocytes in accordance with LARGO (R. LARGO et al., Blood 47, 1976, 991). Furthermore, the test suitable for the diagnosing of von Willebrand's disease based on the precipitator Ristocetin-A (Ristomycin-A) is used for detecting of fibrin monomers (K. WATANABE and J. L. TULLIS, Amer. J. Clin. Pathol. 70, 1978, 691; G. PFLIEGLER et al. Abstr. Int. Congr. ISH-ISBT, Budapest, Aug. 1982, p. 380). Numerous comparative tests have shown that with the above listed precipitators, an nonspecific precipitation with fibrin cleavage products takes place, and with increasing thrombocyte content of the plasma used for detection, falsely positive reactions are obtained so that the reliability of the test is not guaranteed. In addition to the above methods, also various further methods which are connected with expensive analysis techniques are known (affinity chromatography gel-filtration).

SUMMARY OF THE INVENTION

Accordingly, it is an object of the present invention to provide a new test reagent for detecting fibrin monomers in human blood.

It is also an object of the present invention to provide, on the basis of the proposed new test reagent, an economical method of detecting fibrin monomers by precipitation.

In keeping with these objects and with others which will become apparent hereinafter, one feature of the present invention resides, briefly stated, in a test reagent which contains an antibiotic of the pyrrole-amidine series as a precipitator introduced in a buffer solution.

In accordance with an advantageous feature of the present invention, in the new test reagent such pyrrole-amidine series antibiotics as netropsin, distamycin, anthelvencin or analogs introduced in HEPES-buffer are used.

In accordance with a further advantageous feature of the present invention the selected pyrrole-amidine series antibiotic is used in its salt form, for example substantially as its hydrochloride.

Still another feature of the present invention is a method of detecting fibrin monomers in human blood, in accordance with which human blood is mixed with an anticoagulant in a known manner, then centrifuged and the citrate plasma is mixed for precipitation with the above mentioned new test reagent. Then precipitation reaction, or in other words the precipitate sedimented on the bottom of the test vessel, is analyzed in a known manner.

In accordance with still a further feature of the inventive method, the plasma with the precipitant or in other words with the test reagent in accordance with the present invention is maintained under room temperature and subsequently centrifuged.

When the test composition is made and the method is performed in accordance with the present invention, a very cost favorable precipitant can be used such as for example netropsin hydrochloride, and high diagnostic reliability is guaranteed.

DESCRIPTION OF THE PREFERRED EMBODIMENTS

In accordance with the present invention a test reagent contains an antibiotic of the pyrrole-amidine series raw as a precipitant, introduced in a buffer solution. Advantageously, the pyrrole-amidine series antibiotic can be netropsin, distamycin, and anthelvencin or analogs, and the buffer solution can be a HEPES-buffer. The selected pyrrole-amidine series antibiotic can be in its salt form, for example as a hydrochloride.

In accordance with the method of the invention, human blood is mixed in a known manner with an anticoagulant, then centrifuged, and the citrate plasma is mixed for precipitation with the above described new test reagent. Then, the precipitation reaction, or in other words the precipitate sedimented, is analyzed. The plasma provided with the precipitant or in other words with the test reagent of the invention is held under room temperature for the evaluation, and then centrifuged.

The advantages of the inventive solution for detecting fibrin monomers is illustrated by two examples presented hereinbelow:

EXAMPLE I

Venous blood is recovered exactly in accordance with the rules applicable for coagulation tests and citrate plasma is prepared in accordance with conventional methods.

Netropsin-HCl is dissolved in accordance with the requirements in a concentration of 15 mg netropsin/ml with HEPES-buffer (0.15 molar, pH 7.5) so that a test reagent Netropsin RL is produced.

0.4 ml citrate plasma is mixed with 0.1 ml netropsin-RL in a centrifuge tube and is retained for 30 minutes at room temperature. Then this tube is centrifuged for 5 minutes with maximum 50 r.p.m. The precipitate formed on the bottom is evaluated in accordance with the following diagram:

| | |
|---|---|
| flaky loose precipitation | + |
| fibrous deposits | ++ |
| compact sediments | +++ |

The probes evaluated as negative in this manner are transferred to black small block dishes and again evaluated A negative evaluation of course corresponds to fibrin monomers not being detected, while the more positive the evaluation the stronger is the indication of fibrin monomers.

A positive control for comparison is carried for each measuring row.

EXAMPLE II

The preparation, performance and evaluation of the precipitation is carried out as in the Example I. The precipitant in this example is, however, distamycin-HCl, which is dissolved in a concentration of 6 mg/ml in a HEPES-buffer (test reagent Distamycin RL). The sensitivity of this precipitation amounts to approximately 50%, as compared with netropsin.

With the utilization of the inventive test reagent Netropsin RL and the respective methods, the following results were obtained in clinical laboratory tests:

Examination of the testing method for its analytical usefulness.

In vitro produced fibrin monomer containing plasma showed clearly a positive reaction.

From split products of fibrinogens and fibrins (e-FDP, 1-FDP, e-fdp, 1-fdp) recovered in individual preparation, only the fraction of the early fibrin cleavage product (e-fdp) is detected. Since e-fdp is also a product of a thrombin-caused fibrinogen conversion, the specificity of the test is not effected. From a concentration of the low molecular salt products fragment D (0.3 g/l) and fragment E (0.15 g/l) a weakening of the precipitation is observed.

A fibrinogen-dependent influence on the test result could be not found till a plasma fibrinogen concentration of 19 g/l is reached.

An influence of heparin on the precipitation could not be observed.

There was no dependency of the precipitation on thrombocyte content of the used plasma.

There was no influence of plasma expanders upon dextran- and gelatin base.

The test was not influenced by changes in the albumin, alpha-globulin, immunglobulin-G and the total albumin concentration of the plasma.

Examinations for specificity of the test method

The examination of 40 hemostatically healthy hospitalized patients using conventional blood taking techniques for the coagulation test produces a negative test result in all cases (specificity=1.0).

Examination of the Sensitivity of the Test Method 40 patients with clinically and laboratory-diagnostically reliably disseminated intravascular coagulation were subjected to the above described test, and in 37 cases a positive result was achieved. Thereby the method can be considered with a sensitivity of 0.93 as a suitable laboratory parameter for diagnosing of the disseminated intravascular coagulation.

It will be understood that each of the elements described above, or two or more together, may also find a useful application in other types of test combinations and methods differing from the types described above.

While the invention has been illustrated and described as embodied in a test reagent and method it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of detecting the presence of fibrin monomer in blood comprising the steps of:
   a. mixing venous blood with an anticoagulant to form a mixture,
   b. centrifuging said mixture,
   c. removing plasma from said mixture,
   d. mixing said plasma with a test reagent comprising an antibiotic of the pyrrole-amidine series dissolved in a buffer solution to form a reaction mixture, and
   e. evaluating said reaction mixture for the presence of a precipitate indicative of the presence of said fibrin monomer in said blood.

2. The method of claim 1, further comprising before said step of evaluating, allowing said reaction mixture to stand for 30 minutes at room temperature and then centrifuging the same.

3. The method of claim 1, employing said antibiotic selected from the group consisting of netropsin, anthelvencin, distamycin and analogs thereof.

4. The method of claim 1, wherein said buffer is an HEPES-buffer solution.

* * * * *